United States Patent [19]

Meiring et al.

[11] Patent Number: 5,783,176

[45] Date of Patent: Jul. 21, 1998

[54] STABLE HYDROCARBON-FREE COSMETIC ON DERMATOLOGICAL OLEGELS AND W/O EMULSIONS

[75] Inventors: Uta Meiring, Hamburg, Germany; Anne-Sopie Dussert, Toulouse, France; Marta Aul, Hamburg, Germany

[73] Assignee: Beiersdorf AG, Hamburg, Germany

[21] Appl. No.: 744,844

[22] Filed: Nov. 8, 1996

[30] Foreign Application Priority Data

Nov. 10, 1995 [DE] Germany ............... 195 41 968.5

[51] Int. Cl.⁶ .................... A61K 7/40; A61K 7/025
[52] U.S. Cl. .................... 424/64; 424/401; 514/873
[58] Field of Search .................. 424/401, 64; 514/844, 514/845, 846, 847, 873, 937

[56] References Cited

U.S. PATENT DOCUMENTS 5,688,831  11/1997  El-Nokaly et al. ................ 424/59

Primary Examiner—S. Mark Clardy
Assistant Examiner—Robert H. Harrison

Attorney, Agent, or Firm—Sprung Kramer Schaefer & Briscoe

[57] ABSTRACT

Cosmetic formulations which are essentially free from saturated hydrocarbons and comprise (a) a lipid phase comprising at least one glycerol mono-, di- and/or tricarboxylic acid ester of branched and/or unbranched monobasic fatty acids having 18–36 carbon atoms (=mono-, di- and/or triglycerides) and at least one ester chosen from the group consisting of substances having the following structure

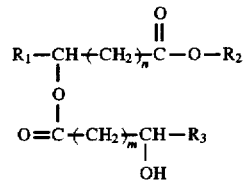

(d) and furthermore, if appropriate, comprise water, further lipids, emulsifiers and customary further active compounds, auxiliaries and/or additives, and the use of such formulations for lip care.

11 Claims, No Drawings

STABLE HYDROCARBON-FREE COSMETIC ON DERMATOLOGICAL OLEGELS AND W/O EMULSIONS

DESCRIPTION

The present invention relates to stable hydrocarbon-free cosmetic or dermatological formulations in the form of oleogels and W/O emulsions. The present invention particularly relates to such a formulation for the purpose of lip care.

Cosmetic skin care is primarily to be understood as intensifying or re-establishing the natural function of the skin as a barrier against environmental influences (for example dirt, chemicals, microorganisms) and against the loss of endogenous substances (for example water, natural fats, electrolytes).

If this function is impaired, increased absorption of toxic or allergenic substances or attack by microorganisms and as a consequence toxic or allergic skin reactions may occur.

The aim of skin care is furthermore to compensate for the loss of fat and water from the skin caused by daily washing. This is particularly important if the natural capacity for regeneration is inadequate. Furthermore, skin care products should provide protection against environmental influences, in particular against sun and wind, and delay ageing of the skin.

Medical topical compositions as a rule comprise one or more medicaments in an active concentration. For simplicity, to make a clear distinction between cosmetic and medical use and corresponding products, reference is made to the legal provisions of the Federal Republic of Germany (for example cosmetics legislation, foodstuff and medical preparations law).

The skin of the lips in particular has only an extremely thin horny layer. There are no sweat glands at all on the lips, and only isolated sebaceous glands are to be found. The skin of the lips is therefore practically free from fat and tends to dry out, especially during cold and dry weather. Small cracks may form in the skin in this case, and the sensitivity of the lips to chemical, physical and microbial actions (for example foods, sunlight, herpes simplex viruses) increases.

To prevent this is the task of lip care formulations, which are usually obtainable in the form of lip care sticks. These products usually comprise a high content of waxes and fat components which, after application, form a covering layer over the lips. Formulations in liquid or semi-solid form, for example lip care gels or creams, are less common but not unusual.

The corium of the lips has papillae with good circulation which extend to just below the lip surface. The lips are therefore reddish in colour and, depending on the complexion of the person in question, stand out in colour from the other skin of the face to a greater or lesser degree. One styling means of decorative cosmetics is also to match the lip colour to the type of person by appropriate cosmetics.

Products of this type are, for example, decorative lipsticks, into which various coloured pigments can be incorporated. These sticks also comprise high contents of waxes and fat components, which form a covering lipid layer over the lips after application.

However, the task of this layer is not meanwhile to protect the skin of the lips from drying out. The lipid layer serves here as a base adhering to the lips for the incorporated pigment substances; the pigments themselves cannot be applied to the lips without such a base for various reasons.

One object of the present invention was to develop formulations for lip care which are distinguished by a high care action and easy handling, and which furthermore would be cosmetically elegant formulations.

Gels are customary cosmetic and dermatological formulation forms which recently have become evermore widespread. Gels are distinguished by a semi-solid, often pourable consistency. Gels are usually transparent or translucent, and occasionally they are even clear. The gel structure is caused by an internal three-dimensional molecular matrix, to which the molecules of an external oily or aqueous phase are loosely bonded by electrostatic interaction. A distinction is essentially made between: oleogels, which are practically anhydrous, hydrogels, which are practically fat-free, and oil/water gels, which ultimately are based on O/W or W/O emulsions in which, however, features of a gel structure are additionally also achieved.

Customary base substances of the prior art are paraffin oils or paraffin waxes, which have the advantage that paraffin-containing recipes, emulsions or oleogels are not particularly unstable to variations in temperature or at least can be stabilized in a simple manner. Paraffins comprise branched and unbranched saturated hydrocarbons of varying chain length.

Omitting paraffin oils and paraffin waxes may be of advantage. For example, the use of chiefly regenerable materials or substances based on such raw materials, the $CO_2$ balance of which is neutral (or at least virtually neutral), in contrast to mineral lipid components, is to be welcomed.

It was also desirable to extend the spectrum of the customary types of formulation to paraffin-free formulations.

In technical terms, almost all lipsticks are anhydrous fat mixtures of solid or semi-solid waxes and liquid oils, the highly purified paraffin oils and waxes representing the lipstick base.

According to the ideal profile of requirements, it should be possible to apply lipsticks smoothly and without a large frictional resistance. Furthermore, a lipstick should not smear or become dull or tacky merely under gentle pressure, but should nevertheless produce a firmly adhering film of fat on the lips. The lips should then be rendered smooth and supple by this film of fat.

A lipstick furthermore must also additionally meet the requirements that it must be break-resistant and heat-resistant and should not release oil.

The customary base substances of the prior art are
(1) liquid oils (for example paraffin oils, castor oil, isopropyl myristate)
(2) semi-solid constituents (for example vaseline, lanolin)
(3) solid constituents (for example beeswax, ceresin and microcrystalline waxes or ozocerite)
(4) high-melting waxes (for example carnauba wax, candelilla wax)

Lipsticks of the prior art with a content of paraffins and beeswax are described in "Kosmetik, Entwicklung Herstellung und Anwendung kosmetischer Mittel" [Cosmetics, development, manufacture and use of cosmetic agents], page 105, editor: W. Umbach, Georg Thieme Verlag, Stuttgart—New York, 1988.

However, the prior art has a number of disadvantages. Thus, DBP 23 35 549 discloses a process for the preparation of a cosmetic stick based on a W/O emulsion. According to this doctrin, a gel is prepared from a polyhydroxy compound and a nonionic, surface-active compound, this gel is mixed with a cosmetic base and a content of water is then emulsified into the mixture.

However, no sticks which have the universal requirements imposed on a cosmetic stick are to be produced by this process.

Another disadvantage is that up until the current point in time, paraffin oils and waxes were indispensable constituents for lipsticks. Although these are raw materials which are obtainable in a good quality, a stick with usable properties can be formulated with their aid, the use properties of such cosmetic sticks are limited. Furthermore, paraffins are valuable base substances, the occurrences of which on earth are limited. Modern production is progressing in the direction of regenerable raw materials, that is to say, for example, vegetable waxes or oils, in the field of cosmetics.

However, it was impossible to date to design a cosmetic stick based on the known vegetable waxes, fats or oils or chemically modified vegetable waxes, fats or oils. Another object of the present invention was thus to provide a base for cosmetic sticks, in particular lipsticks, which can dispense with mineral oils and instead can be based on vegetable or, where appropriate, animal lipid components or chemically modified variants thereof.

Overall, the object of the invention was thus to develop formulations which remedy the disadvantages of the prior art in this respect.

Astonishingly, and therein lies the achievement of all these objects, cosmetic formulations which are essentially free from saturated hydrocarbons and comprise (a) a lipid phase comprising at least one glycerol mono-, di- and/or tricarboxylic acid ester of branched and/or unbranched monobasic fatty acids having 18–36 carbon atoms (=mono-, di- and/or triglycerides) and at least one ester chosen from the group consisting of substances having the following structure

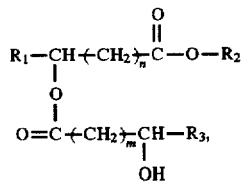

wherein

R1 and R3 independently of one another are a branched or unbranched saturated hydrocarbon radical having 3–30 carbon atoms and R2 is a branched or unbranched saturated hydrocarbon radical having 5–50 carbon atoms, and n and m independently of one another assume values from 5 to 25.

(d) and furthermore, if appropriate, comprise water, further lipids, emulsifiers and customary further active compounds, auxiliaries and/or additives, remedy the disadvantages of the prior art.

A particular embodiment of the present invention is the use of cosmetic formulations which are essentially free from saturated hydrocarbons and comprise (a) a lipid phase comprising at least one glycerol mono-, di- and/or tricarboxylic acid ester of branched and/or unbranched monobasic fatty acids having 18–36 carbon atoms (=mono-, di- and/or triglycerides) and at least one ester chosen from the group consisting of substances having the following structure

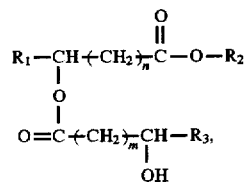

wherein

R1 and R3 independently of one another are a branched or unbranched saturated hydrocarbon radical having 3–30 carbon atoms and R2 is a branched or unbranched saturated hydrocarbon radical having 5–50 carbon atoms, and n and m independently of one another assume values from 5 to 25.

(d) and furthermore, if appropriate, comprise water, further lipids, emulsifiers and customary further active compounds, auxiliaries and/or additives, as a lip care formulation.

The formulations according to the invention can advantageously be in the form of oleogels, in which case in essentially anhydrous form, or W/O emulsions. They are distinguished by a high heat-stability, excellent adhesion and very good use properties. It is also possible and advantageous to develop the formulations according to the invention in the form of cosmetic sticks.

The mono-, di- and/or triglyceride or -glycerides is or are advantageously present according to the invention in a content of 0.5–10% by weight, based on the total weight of the formulations. The ester or esters chosen from the group of substances having the following structure

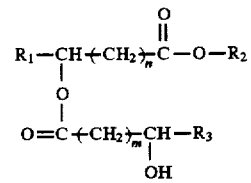

is or are advantageously present in a content of 15–25% by weight, based on the total weight of the formulations.

Preferred lipid components are chosen from the group consisting of mono-, di- and triglycerides and of esters chosen from the group consisting of substances having the following structure

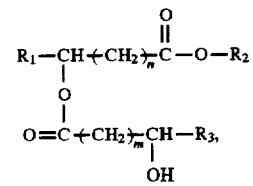

wherein

R1 and R3 independently of one another are a branched or unbranched saturated hydrocarbon radical having 5–10 carbon atoms and R2 is a branched or unbranched saturated hydrocarbon radical having 5–50 carbon atoms, and n and m independently of one another assume values from 5 to 15.

Preferred esters are the C19–39-alkyl hydroxystearoyl-stearates.

The features of the present invention are advantageously realized if the lipid phase comprises liquid lipids to the extent of 10–90% by weight, preferably 50–70% by weight, semi-solid lipids to the extent of 0.5–90% by weight, preferably 5–30% by weight, and solid lipids to the extent of 0.5–50% by weight, preferably 25–40% by weight, in each case based on the total weight of the formulations.

If it is desired to develop the formulations according to the invention as W/O emulsions, the water content can advantageously be 0.1–15% by weight, preferably 3–5% by weight, in each case based on the total weight of the formulations.

The following can be employed as W/O emulsifiers which are optional but nevertheless advantageous according to the invention: monoglycerol esters of saturated and/or unsaturated, branched and/or unbranched alkane carboxylic acids having a chain length of 8 to 24, in particular 12–18, C atoms, diglycerol esters of saturated and/or unsaturated, branched and/or unbranched alkane-carboxylic acids having a chain length of 8 to 24, in particular 12–18, C atoms, triglycerol esters of saturated and/or unsaturated, branched and/or unbranched alkanecarboxylic acids having a chain length of 8 to 24, in particular 12–18, C atoms, monoglycerol ethers of saturated and/or unsaturated, branched and/or unbranched alcohols having a chain length of 8 to 24, in particular 12–18, C atoms, diglycerol ethers of saturated and/or unsaturated, branched and/or unbranched alcohols having a chain length of 8 to 24, in particular 12–18, C atoms, triglycerol ethers of saturated and/or unsaturated, branched and/or unbranched alcohols having a chain length of 8 to 24, in particular 12–18, C atoms, propylene glycol esters of saturated and/or unsaturated, branched and/or unbranched alkanecarboxylic acids having a chain length of 8 to 24, in particular 12–18, C atoms and sorbitan esters of saturated and/or unsaturated, branched and/or unbranched alkanecarboxylic acids having a chain length of 8 to 24, in particular 12–18, C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, polyglyceryl 2-polyhydroxystearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, behenyl alcohol, isobehenyl alcohol, selachyl alcohol and chimyl alcohol.

If the present invention is realized in cosmetic sticks in particular, it may be advantageous to use beeswax and/or esters of saturated branched or unbranched aliphatic carboxylic acids having 14–44 carbon atoms and saturated branched or unbranched aliphatic alcohols having 14–44 carbon atoms as further constituents.

If appropriate, the aqueous phase of the formulations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol, and, in particular, one or more thickening agents, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of so-called carbopoles, for example carbopoles of types 980, 981, 1382, 2984 or 5984, or also of the ETD (easy-to-disperse) types 2001, 2020 and 2050, in each case individually or in any desired combinations with one another.

Particularly advantageous formulations are furthermore obtained if antioxidants are employed as additives or active compounds. According to the invention, the formulations advantageously comprise one or more antioxidants. All the antioxidants suitable or customary for cosmetic and/or dermatological uses can be used as antioxidants which are favourable but nevertheless optionally to be used.

The antioxidants are advantageously chosen from the group consisting of amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to µmol/kg), and furthermore (metal) chelators (for example α-hydroxy-fatty acids, palmitic acid, phytic acid or lactoferrin), α-hydroxy acids (for example citric acid, lactic acid and maleic acid), humic acid, bile acid, bile extracts, bilirubin, biliverdin, EDTA, EGTA and derivatives thereof, and unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoic resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

Oil-soluble antioxidants can be particularly advantageously employed in the context of the present invention.

One astonishing property of the present invention is that formulations according to the invention are very good vehicles for cosmetic or dermatological active compounds in the skin, preferred active compounds being antioxidants which can protect the skin against exposure to oxidation. Preferred antioxidants here are vitamin E and derivatives thereof and vitamin A and derivatives thereof.

The amount of antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, bases on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

It is of course known to the expert that high-quality cosmetic formulations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellents, alcohol, water, salts, substances having an antimicrobial, proteolytic or keratolytic action and the like.

Mutatis mutandis, corresponding requirements apply to the formulation of medicinal formulations.

The formulations according to the invention advantageously comprise at least one UVA filter substance and/or at least one UVB filter substance and/or at least one inorganic pigment.

However, it is also advantageous, in the context of the present invention, to compile those cosmetic and dermatological formulations of which the chief purpose is not protection from sunlight but which nevertheless comprise a content of UV protection substances. Thus, for example, UV-A or UV-B filter substances are usually incorporated into vanishing creams.

UV protection substances, like antioxidants and, if desired, preservatives, also represent active protection of the formulations themselves against decay.

Formulations according to the invention can advantageously furthermore comprise substances which absorb UV radiation in the UVB range, the total amount of filter substances being, for example, 0.1% by weight to 30% by weight, preferably 0.5 to 10% by weight, in particular 1.0 to 6.0% by weight, based on the total weight of the formulations, in order to provide cosmetic formulations which protect the skin from the entire range of ultraviolet radiation. They can also be used as sunscreen agents for the hair or the skin.

If the emulsions according to the invention comprise UVB filter substances, these can be oil-soluble or water-soluble. Oil-soluble UVB filters which are advantageous according to the invention are, for example:

3-benzylidenecamphor derivatives, preferably 3-(4-methylbenzylidene) camphor and 3-benzylidenecamphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate, derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate;

2,4,6-trianilino-(p-carbo-2'-ethyl-1'-hexyloxy)1,3,-5-triazine.

Advantageous water-soluble UVB filters are, for example:

salts of 2-phenylbenzimidazole-5-sulphonic acid, such as its sodium, potassium or its triethanolammonium salt, and 2-phenylbenzimidazole-5-sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and their salts.

The list of UVB filters mentioned, which can be used in combination with the active compound combinations according to the invention, is of course not intended to be limiting.

It may also be advantageous to formulate lipodispersions according to the invention with UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological formulations according to the invention can also comprise inorganic pigments which are usually used in cosmetics for protection of skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide.

The cosmetic and dermatological formulations according to the invention can furthermore comprise cosmetic auxiliaries such as are usually used in such formulations, for example preservatives, bactericides, virusides, perfumes, substances for preventing foaming, dyestuffs, pigments which have a colouring action, thickening agents, surface-active substances, emulsifiers, softening, moistening and/or humectant substances, anti-inflammatory-substances, medicaments, fats, oils, waxes or other customary constituents of a cosmetic or dermatological formulation, such as alcohols, polyols, polymers, foam stabilizers, electrolytes and organic solvents.

Further constituents which can be used are:

fats, waxes and other naturally occurring and synthetic fat substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

The following examples are intended to illustrate the present invention.

EXAMPLES 1–6

Polar Lip Gels with a High Fat Content

Lip gel 1

| | |
|---|---|
| Tribehenin | 4.0 |
| $C_{19-39}$ alkyl hydroxystearoyl stearate | 25.0 |
| Capylic/capric acid triglyceride | 10.0 |
| 2-octyldodecanol | 10.0 |
| Castor oil | 34.0 |
| Bis-diglyceryl caprylate/caprate/isostearate/stearate/hydrogenated adipate | 5.0 |
| 2-ethylhexyl palmitate | 12.0 |

Lip gel 2

| | |
|---|---|
| Behenyl alcohol | 3.5 |
| $C_{19-39}$ alkyl hydroxystearoyl stearate | 20.0 |
| Caprylic/capric acid triglyceride | 15.0 |
| 2-octyldodecanol | 14.0 |
| Castor oil | 30.0 |
| Shea butter | 10.0 |
| Avocadin | 1.0 |
| Beeswax | 1.5 |

Lip gel 3

| | |
|---|---|
| Tribehenin | 2.0 |
| $C_{18-36}$ wax acid glyceryl ester | 2.0 |
| $C_{19-39}$ alkyl hydroxystearoyl stearate | 15.0 |
| Jojoba oil | 5.0 |
| Dicaprylyl ether | 10.0 |
| Castor oil | 40.0 |
| bis-diglyceryl caprylate/caprate/isostearate/stearate/hydrogenated adipate | 8.0 |
| Myristyl myristate | 3.0 |
| Decyl oleate | 5.0 |
| Cetearyl isononanoate | 5.0 |
| Paraffin oil | 5.0 |

Lip gel 4

| | |
|---|---|
| Tribehenin | 2.0 |
| Behenyl alcohol | 1.5 |
| $C_{15-29}$ alkyl hydroxystearoyl stearate | 20.0 |
| Caprylic/capric acid triglyceride | 20.0 |
| 2-octyldodecanol | 10.0 |
| Castor oil | 20.0 |
| Bis-diglyceryl caprylate/caprate/isostearate/stearate/hydrogenated adipate | 5.0 |
| Shea butter | 5.0 |
| Cetostearyl alcohol | 1.5 |
| Macadamia nut oil | 5.0 |
| Glycerol | 5.0 |

Lip gel 5

| | |
|---|---|
| Tribehenin | 1.5 |
| $C_{18-36}$ wax acid glyceryl ester | 1.0 |
| Behenyl alcohol | 1.5 |
| $C_{29-49}$ alkyl hydroxystearoyl stearate | 12.0 |
| Caprylic/capric acid triglyceride | 20.0 |
| Cetearyl octanoate/isopropyl myristate | 10.0 |
| Castor oil | 30.0 |
| Octyl methoxy cinnamate | 2.0 |
| Shea butter | 4.75 |
| Wool wax alcohols | 1.0 |
| Cetyl palmitate | 1.0 |
| Beeswax | 1.5 |
| Water | 5.0 |
| Glycerol | 5.0 |
| Triglyceryldi-isostearate | 3.75 |

Lip gel 6

| | |
|---|---|
| Tribehenin | 1.0 |
| $C_{18-36}$ wax acid glyceryl ester | 1.0 |
| Castor oil, hydrogenated | 2.0 |
| $C_{19-39}$ alkyl hydroxystearoyl stearate | 18.0 |
| Caprylic/capric acid triglyceride | 10.0 |
| 2-Octyldodecanol | 10.0 |
| Castor oil | 30.0 |
| Bis-glyceryl caprylate/caprate/isostearate/stearate/hydrogenated adipate | 5.0 |
| Shea butter | 3.0 |
| Dicaprylyl ether | 10.0 |
| Carbomer | 0.035 |
| NaOH 45% strength | 0.0185 |
| Water | 4.9465 |
| Glycerol | 5.0 |

The fat components are melted at 90°–95° C. In a separate operation, the aqueous phase is heated to 70° C. and then added to the fat phase, while stirring. The mass is cooled, while stirring.

EXAMPLES 7–9

Stick Formulations

Stick 1

| | |
|---|---|
| medium-polar | |
| Tribehenin | 1.0% |
| $C_{19-39}$ alkyl hydroxystearoyl stearate | 1.0% |
| Carnauba wax | 1.3% |
| Shea butter | 1.5% |
| Myristyl myristate | 9.0% |
| Ceresin | 12.0% |
| Cetostearyl alcohol | 2.5% |
| Hydrogenated | 5.0% |

| | | |
|---|---|---|
| coconut fatty acid glycerides | | |
| Ozocerite | 6.0% | |
| Caprylic/capric acid triglyceride | 26.7% | |
| Castor oil | 12.0% | |
| Dicaprylyl ether | 22.0% | |
| Stick 2 | | |
| medium-polar | | |
| Tribehenin | 1.0% | |
| $C_{19-39}$ alkyl hydroxystearoyl stearate | 0.5% | |
| Carnauba wax | 1.6% | |
| $C_{18-36}$ wax acid glyceryl ester | 1.0% | |
| Myristyl myristate | 10.0% | |
| Ceresin | 22.4% | |
| Cetostearyl alcohol | 2.5% | |
| Caprylic/capric acid triglyceride | 22.0% | |
| Castor oil | 12.0% | |
| 2-Octyldodecanol | 27.0% | |
| Stick 3 | | |
| polar | | |
| Tribehenin | 2.5% | |
| $C_{19-39}$ alkyl hydroxystearoyl stearate | 2.5% | |
| Carnauba wax | 2.5% | |
| Shea butter | 2.5% | |
| Jojoba wax, hydrogenated | 4.5% | |
| Candelilla wax | 6.0% | |
| Bis-diglyceryl caprylate/caprate/isostearate/stearate/hydrogenated adipate | 8.0% | |
| Hydrogenated coconut fatty acid glycerides | 3.0% | |
| Beeswax | 5.0% | |
| Caprylic/capric acid triglyceride | 10.0% | |
| Castor oil | 13.5% | |
| Dicapryl ether | 20.0% | |
| Jojoba oil | 4.0% | |
| Avocado oil | 4.0% | |
| Macadamia nut oil | 4.0% | |
| Squalane | 4.0% | |
| Mango core fat | 2.0% | |
| Cholesteryl/behenyl/octyldodecyl lauroylglutamate | 2.0% | |

The fat components are melted at 90°–95° C. The mass cools to 70° C., while stirring, and is then poured.

EXAMPLES 10–14

W/O emulsions

| | | |
|---|---|---|
| Emulsion 1 | | |
| polar fat phase | | |
| Tribehenin | 1.0% | |
| $C_{19-39}$ alkyl hydroxystearoyl stearate | 4.0% | |
| Triglyceryl diisostearate | 3.0% | |
| Polyglyceryl 2-polyhydroxystearate | 3.0% | |
| Isopropyl stearate | 4.0% | |
| Polyisobutene | 2.0% | |
| Caprylic/capric acid triglyceride | 3.5% | |
| Macadamia nut oil | 1.5% | |
| Octyl cocoate | 5.6% | |
| Phenoxy ethanol | 0.4% | |
| Methyl paraben | 0.18% | |
| Propyl paraben | 0.02% | |
| Glycerol | 3.0% | |
| $MgSO_4$ | 0.7% | |
| Water | 68.1% | |
| Emulsion 2 | | |
| medium-polar | | |
| Tribehenin | 1.5% | |
| $C_{19-29}$ alkyl hydroxystearoyl stearate | 2.0% | |
| Triglyceryl diisostearate | 2.4% | |
| Dicocoylpentaerythrityldistearyl citrate | 1.2% | |
| Squalane | 10.0% | |
| Cetearyl octanoate/isopropyl myristate | 5.0% | |
| Ceatearyl isononanoate | 5.0% | |
| Phenoxy ethanol | 0.4% | |
| Methyl paraben | 0.18% | |
| Propyl paraben | 0.02% | |
| Glycerol | 3.0% | |
| $MgSO_4$ | 0.7% | |
| Water | 68.7% | |
| Emulsion 3 | | |
| medium-polar | | |
| Tribehenin | 0.75% | |
| $C_{19-39}$ alkyl hydroxystearoyl stearate | 3.0% | |
| Triglyceryl diisostearate | 2.4% | |
| Dicocoylpentaerythrityldistearyl citrate | 1.2% | |
| Squalane | 12.0% | |
| Decyl ole- | 5.0% | |

| | |
|---|---|
| ate | |
| Shea butter | 6.5% |
| Phenoxy ethanol | 0.4% |
| Methyl paraben | 0.18% |
| Propyl paraben | 0.02% |
| Glycerol | 3.0% |
| MgSO$_4$ | 0.7% |
| Water | 64.85% |

Emulsion 4 medium-polar

| | |
|---|---|
| Tribehenin | 0.5% |
| C$_{19-39}$ alkyl hydroxy stearoyl stearate | 4.0% |
| Glyceryl sorbitan fatty acid ester | 3.0% |
| Glyceryl isostearate | 2.0% |
| Polydecene | 10.0% |
| Octyl cocoate | 5.5% |
| Cetearyl isononanoate | 3.5% |
| Phenoxy ethanol | 0.4% |
| Methyl paraben | 0.18% |
| Propyl paraben | 0.02% |
| Glycerol | 3.0% |
| MgSO$_4$ | 0.7% |
| Water | 67.2% |

The fat phase is heated to 85° C. until the solid constituents have melted. The aqueous phase is heated separately to 75° C. and added to the fat phase, while stirring. The emulsion cools to 35° C., while stirring, and is then homogenized.

EXAMPLE 14

Cold Protection Cream

| | |
|---|---|
| Tribehenin | 3.5% |
| C$_{19-39}$ alkyl hydroxystearoyl stearate | 20.0% |
| Bis-diglyceryl caprylate/caprate/isostearate/stearate/ hydrogenated adipate | 3.5% |
| Caprylic/capric acid triglyceride | 8.0% |
| 2-Octyldodecanol | 8.0% |
| Dicaprylyl ether | 6.0% |
| 2-Ethylhexyl palmitate | 6.0% |
| Castor oil | 32.0% |
| Avocadin | 2.5% |
| Bisabolol | 0.5% |
| Zinc oxide | 5.0% |
| Talc | 5.0% |

EXAMPLE 15

Baby Wound Cream

| | |
|---|---|
| Tribehenin | 3.0% |
| C$_{19-39}$ alkyl hydroxystearoyl stearate | 18.5% |
| Wool wax alcohols | 1.0% |
| Glyceryl lanolate | 2.0% |
| Shea butter | 5.0% |
| Caprylic/capric acid triglyceride | 10.0% |
| 2-Octyldodecanol | 10.0% |
| Castor oil | 23.5% |
| Bisabolol | 1.0% |
| Titanium dioxide | 3.0% |
| Zinc oxide | 5.0% |
| Kaolin | 13.0% |
| Talc | 5.0% |

4) and 5) The fat components are melted at 90°–95° and the pigments are then stirred in and dispersed with the Turrax.

We claim:

1. Cosmetic formulations which comprise (a) a lipid phase comprising at least one glycerol mono-, di- and/or tricarboxylic acid ester of branched and/or unbranched monobasic fatty acids having 18–36 carbon atoms (=mono-, di- and/or triglycerides) and at least one ester prepared from a hydroxycarboxylic acid and a branched or unbranched saturated alcohol having 15–49 carbon atoms.

(d) and optionally comprise water, further lipids, emulsifiers and further active compounds, auxiliaries and/or additives.

2. Formulations according to claim 1 or wherein the mono-, di- and/or triglyceride or -glycerides is or are present in a content of 2.5–5% by weight, in each case based on the total weight of the formulations.

3. Formulations according to claim 1 wherein the ester or esters chosen from the group of substances having the following structure

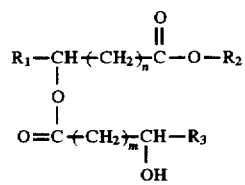

is or are present in a content of 15–25% by weight, in each case based on the total weight of the formulations.

4. Formulations according to claim 1 wherein the lipid phase comprises liquid lipids to the extent of 10–90% by weight, by weight, semi-solid lipids to the extent of 0.5–90% by weight, and solid lipids to the extent of 0.5–50% by weight, in each case based on the total weight of the formulations.

5. Formulations according to claim 1 wherein the water content is 0.1–15% by weight, based on the total weight of the formulations.

6. A method for caring of the lip which comprises applying to said lip an effective amount of a cosmetic formulation which comprises (a) a lipid phase comprising at least one glycerol mono-, di- and/or tricarboxylic acid ester of branched and/or unbranched monobasic fatty acids having 18–36 carbon atoms (=mono-, di- and/or triglycerides) and at least one ester chosen from the group consisting of substances having the following structure

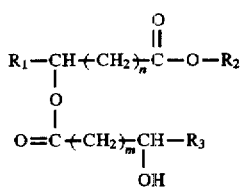

wherein
- $R^1$ and $R^3$ independently of one another are a branched or unbranched saturated hydrocarbon radical having 3–30 carbon atoms and $R^2$ is a branched or unbranched saturated hydrocarbon having 5–50 carbon atoms, and n and m independently of one another assume values from 5 to 25,
- (d) and which optionally comprises water, further lipids, emulsifiers and further active compounds, auxiliaries and/or additives as a lip care.

7. A method for caring of the lip which comprises applying to said lip an effective amount of a cosmetic formulation according to claim 1.

8. Formulations according to claim 1, wherein the lipid phase comprises liquid lipids to the extent of 50–70% by weight based on the total weight of the formulations.

9. Formulations according to claim 1, wherein the lipid phase comprises semi-solid lipids to the extent of 5–30% by weight based on the total weight of the formulations.

10. Formulations according to claim 1, wherein the lipid phase comprises solid lipids to the extent of 25–40% by weight, based on the total weight of the formulations.

11. Formulations according to claim 1, wherein the water content is 3–5% by weight, based on the total weight of the formulations.

* * * * *

UNITED STATES PATENT AND TRADEMARK OFFICE
CERTIFICATE OF CORRECTION

PATENT NO.   :  5,783,176
DATED        :  July 21, 1998
INVENTOR(S)  :  Uta Meiring, et al.

It is certified that error appears in the above-identified patent and that said Letters Patent is hereby corrected as shown below:

| | |
|---|---|
| Title Page [54], Title and Col. 1, Line 2 | Line 2 delete "ON" and substitute -- or --; delete " OLEGELS" and substitute -- OLEOGELS -- |
| Col. 14, Line 24 | Delete "15-49" and substitute -- 5-50 -- |
| Column 14, Line 5 | After "and" and before "optionally" insert -- which -- |
| Col. 14, Line 51 | After "weight" (first occurrence) delete -- by weight -- |

Signed and Sealed this

Eighth Day of February, 2000

Attest:

Q. TODD DICKINSON

Attesting Officer

Commissioner of Patents and Trademarks